US010837661B2

(12) United States Patent
Samuel, Jr.

(10) Patent No.: US 10,837,661 B2
(45) Date of Patent: Nov. 17, 2020

(54) AIR PURIFYING DEVICE

(71) Applicant: Carl Samuel, Jr., Bronx, NY (US)

(72) Inventor: Carl Samuel, Jr., Bronx, NY (US)

(*) Notice: Subject to any disclaimer, the term of this patent is extended or adjusted under 35 U.S.C. 154(b) by 169 days.

(21) Appl. No.: 16/149,129

(22) Filed: Oct. 2, 2018

(65) Prior Publication Data
US 2020/0103126 A1 Apr. 2, 2020

(51) Int. Cl.
*A61L 9/16* (2006.01)
*F24F 3/16* (2006.01)
*F24F 13/20* (2006.01)
*F24F 13/28* (2006.01)

(52) U.S. Cl.
CPC ............ *F24F 3/1603* (2013.01); *A61L 9/16* (2013.01); *F24F 3/166* (2013.01); *F24F 13/20* (2013.01); *F24F 13/28* (2013.01); *A61L 2209/14* (2013.01); *F24F 2221/02* (2013.01)

(58) Field of Classification Search
None
See application file for complete search history.

(56) References Cited

U.S. PATENT DOCUMENTS

| | | | | |
|---|---|---|---|---|
| 3,936,284 A | * | 2/1976 | Mason | B01D 46/12 96/117.5 |
| 4,171,210 A | * | 10/1979 | Miller | B01D 46/10 160/371 |
| 4,370,155 A | * | 1/1983 | Armbruster | B01D 46/12 454/230 |
| 5,407,469 A | * | 4/1995 | Sun | B03C 3/011 361/226 |
| 5,443,625 A | * | 8/1995 | Schaffhausen | B01D 46/0005 95/113 |
| D394,100 S | * | 5/1998 | Promseeda | D23/355 |
| 7,535,341 B2 | | 5/2009 | Haase | |
| 8,218,805 B2 | | 7/2012 | Hornback | |
| D745,954 S | | 12/2015 | de Siqueira Indio da Costa | |
| 9,308,289 B2 | | 4/2016 | Graff | |
| 9,415,341 B2 | | 8/2016 | Nakamura et al. | |
| 9,759,438 B2 | | 9/2017 | Cur | |
| 2016/0121251 A1 | | 5/2016 | Baek | |
| 2016/0138792 A1 | * | 5/2016 | Wang | F21V 33/0052 362/253 |
| 2018/0320887 A1 | * | 11/2018 | Veltri | G02B 5/08 |

FOREIGN PATENT DOCUMENTS

KR 20180125833 A * 11/2018

OTHER PUBLICATIONS

Machine translation for KR 20180125833 A. Retrieved from EPO website on May 12, 2020 (Year: 2020).*

* cited by examiner

Primary Examiner — Jennifer A Leung

(57) ABSTRACT

An air purifying device for providing clean air and entertainment includes a housing that defines an interior space. A plurality of couplers is coupled to a back of the housing and is configured to couple the housing to a vertical surface. A set of first slots and set of second slots are positioned in the housing and are configured for air to enter and exit the interior space, respectively. A plurality of filters and a blower module are coupled to the housing and are positioned in the interior space. The blower module is configured to draw the air through the first slots and the filters. The air is filtered and expelled from the housing through the second slots.

18 Claims, 5 Drawing Sheets

AIR PURIFYING DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relate to purifying devices and more particularly pertains to a new purifying device for providing clean air and entertainment.

BRIEF SUMMARY OF THE INVENTION

An embodiment of the disclosure meets the needs presented above by generally comprising a housing that defines an interior space. A plurality of couplers is coupled to a back of the housing and is configured to couple the housing to a vertical surface. A set of first slots and set of second slots are positioned in the housing and are configured for air to enter and exit the interior space, respectively. A plurality of filters and a blower module are coupled to the housing and are positioned in the interior space. The blower module is configured to draw the air through the first slots and the filters. The air is filtered and expelled from the housing through the second slots.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
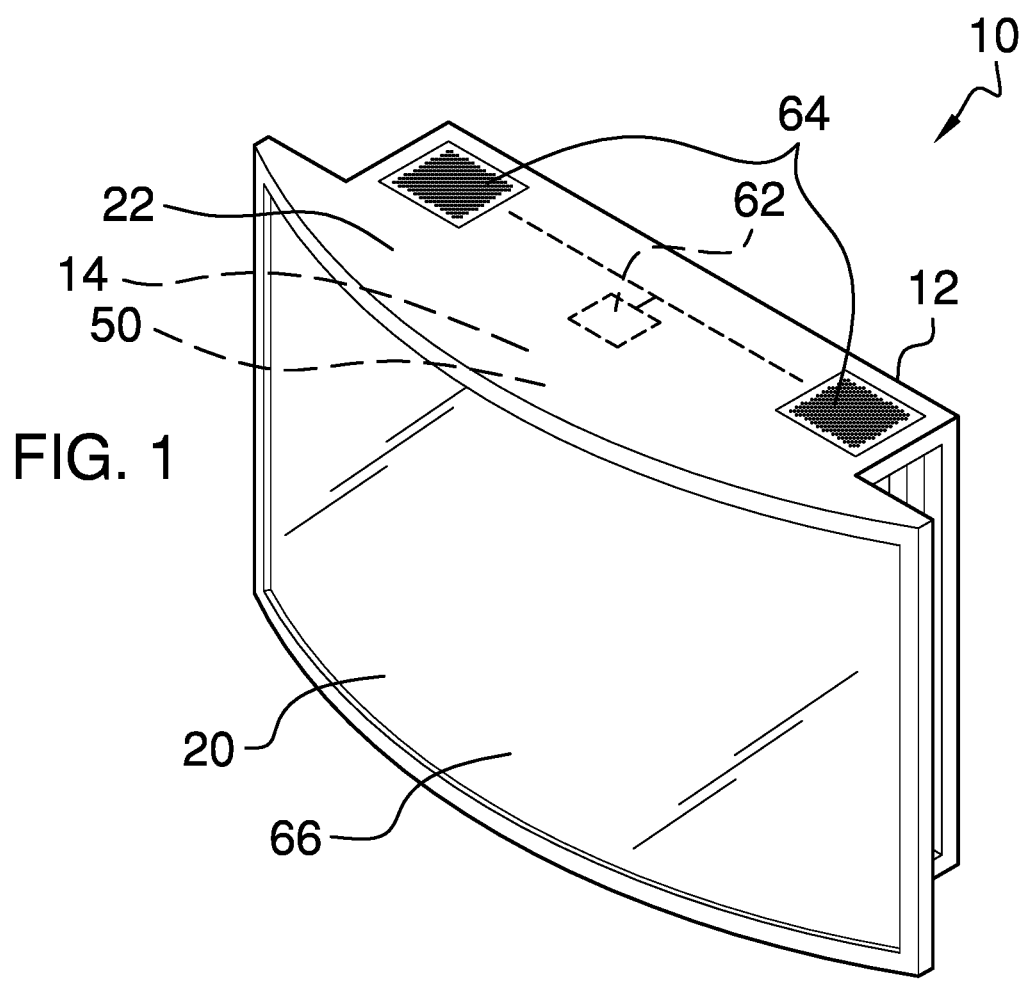
FIG. 1 is an isometric perspective view of an air purifying device according to an embodiment of the disclosure.
Figure 2:
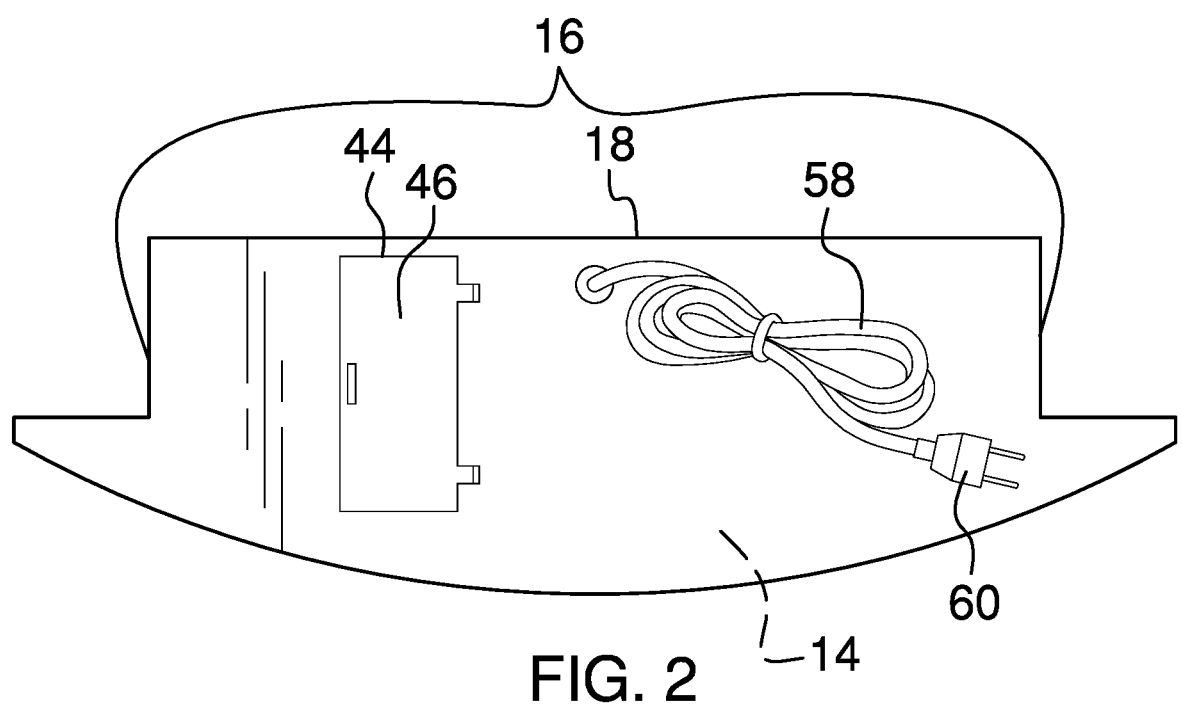
FIG. 2 is a bottom view of an embodiment of the disclosure.

With reference now to the drawings, and in particular to FIGS. 1 through 6 thereof, a new purifying device embodying the principles and concepts of an embodiment of the disclosure and generally designated by the reference numeral 10 will be described.

As best illustrated in FIGS. 1 through 6, the air purifying device 10 generally comprises a housing 12 that defines an interior space 14. The housing 12 is substantially rectangularly box shaped. The housing 12 has opposing sides 16 that are recessed from a back 18 of the housing 12 to proximate to a front 20 of the housing 12, and from a top 22 to a bottom 24 of the housing 12. The front 20 of the housing 12 is convexly arcuate.

A plurality of couplers 26 is coupled to the back 18 of the housing 12. The couplers 26 are configured to couple the housing 12 to a vertical surface, such as an interior wall of a room. The plurality of couplers 26 comprises two couplers 26, each of which comprises a keyhole slot 28. The keyhole slot 28 is configured to insert an article of mounting hardware, such as a nail, a screw, or the like, to couple the housing 12 to the vertical surface.

Figure 3:
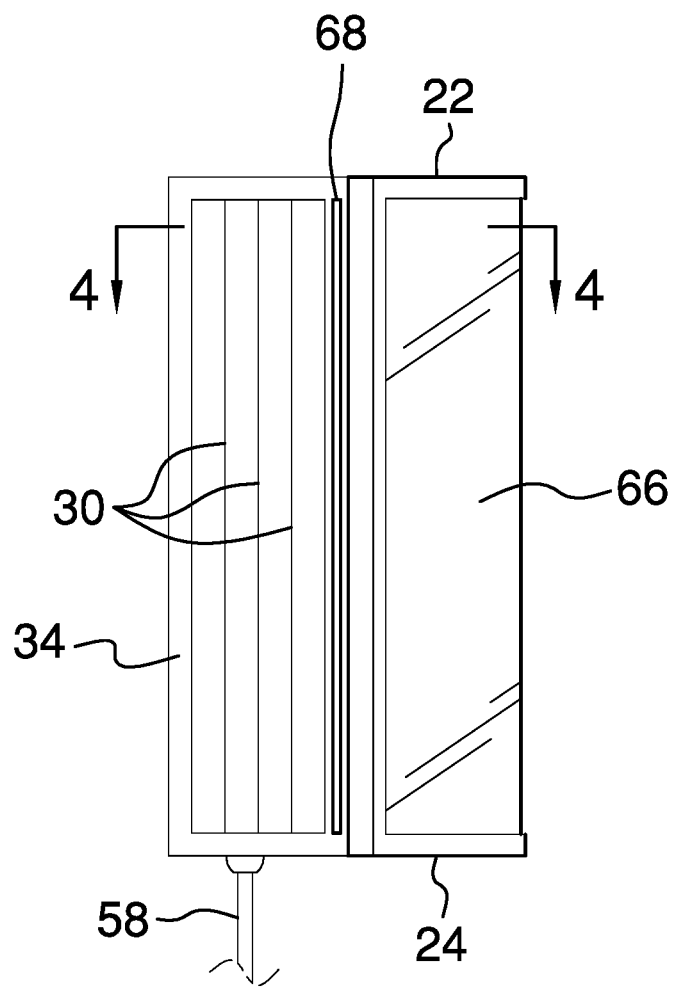
FIG. 3 is a side view of an embodiment of the disclosure.

A set of first slots 30 is positioned in the housing 12 and is configured to allow air to enter the interior space 14. A set of second slots 32 is positioned in the housing 12 and is configured to allow the air to exit the interior space 14. The first slots 30 and the second slots 32 louvered, as shown in FIG. 3. The first slots 30 are positioned in a first opposing side 34 of the housing 12 and the second slots 32 are positioned in a second opposing side 36 of the housing 12.

Figure 4:
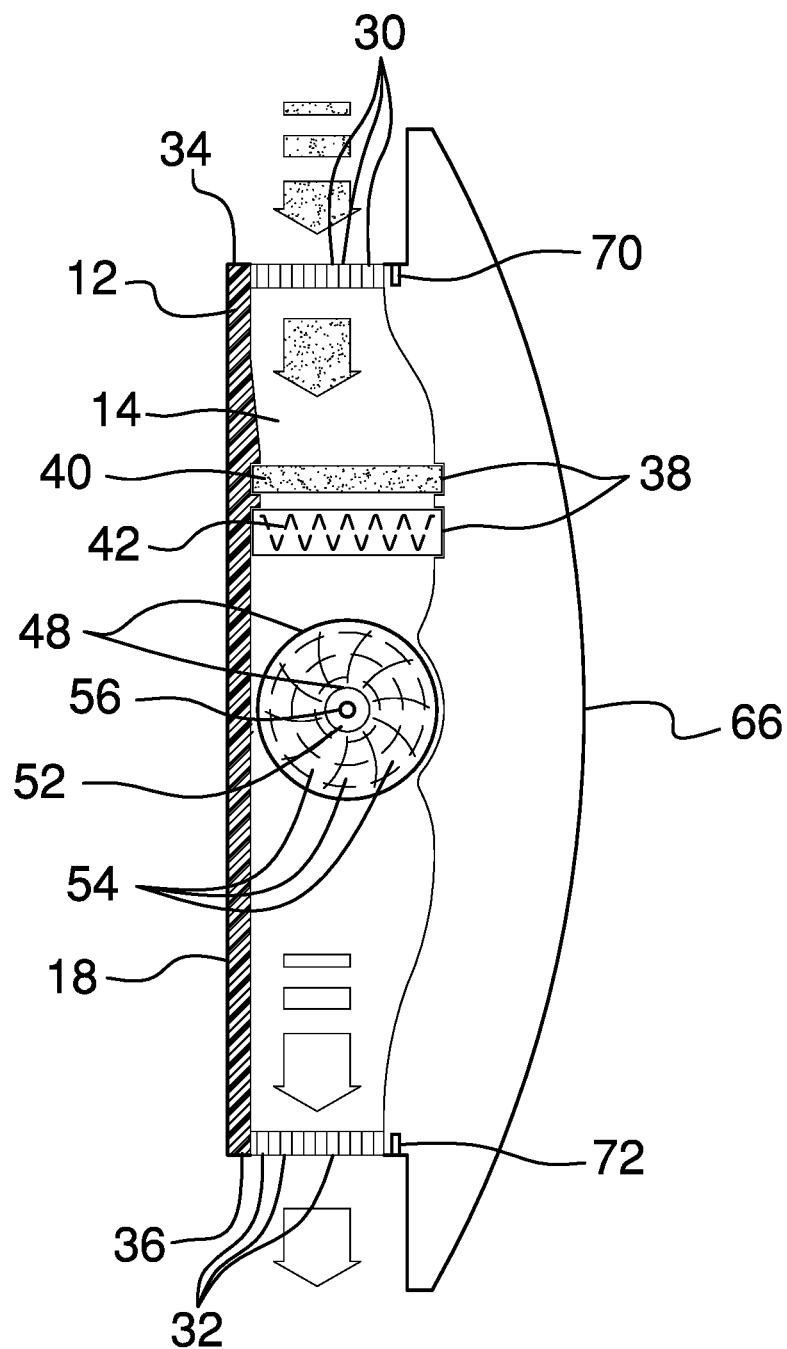
FIG. 4 is a cross-sectional view of an embodiment of the disclosure.
Figure 5:
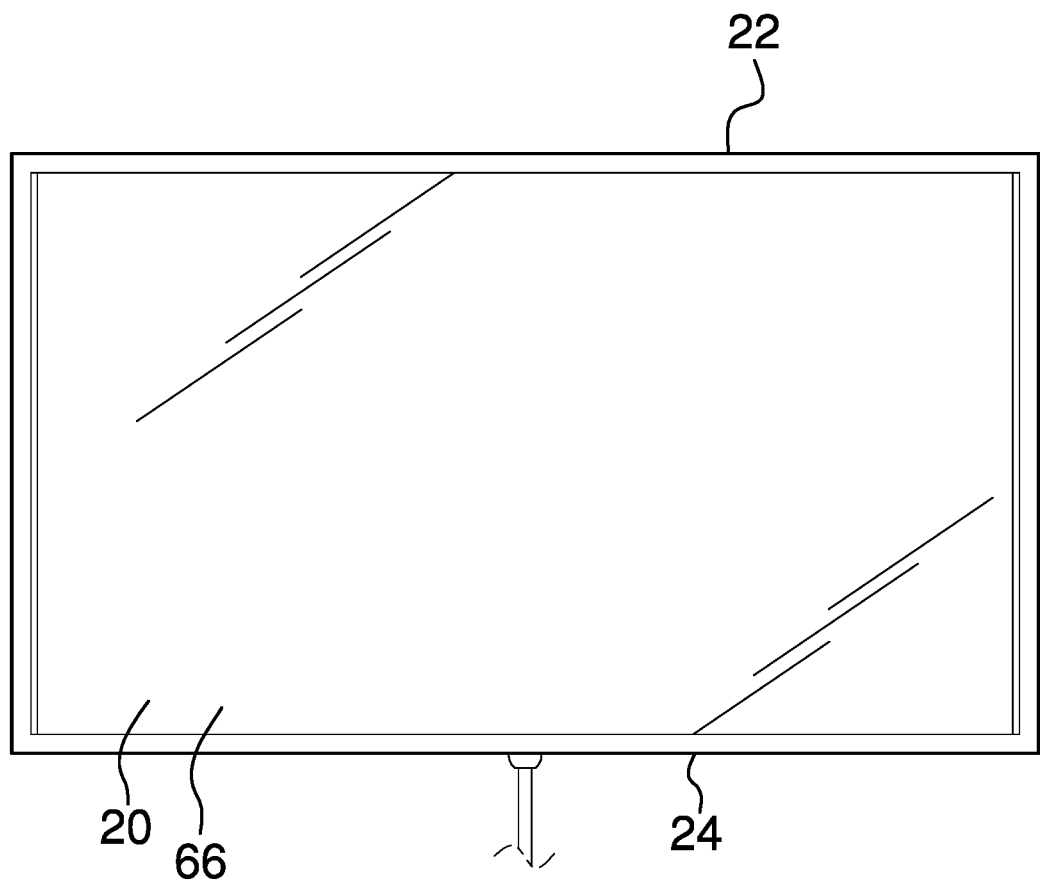
FIG. 5 is a front view of an embodiment of the disclosure.
Figure 6:
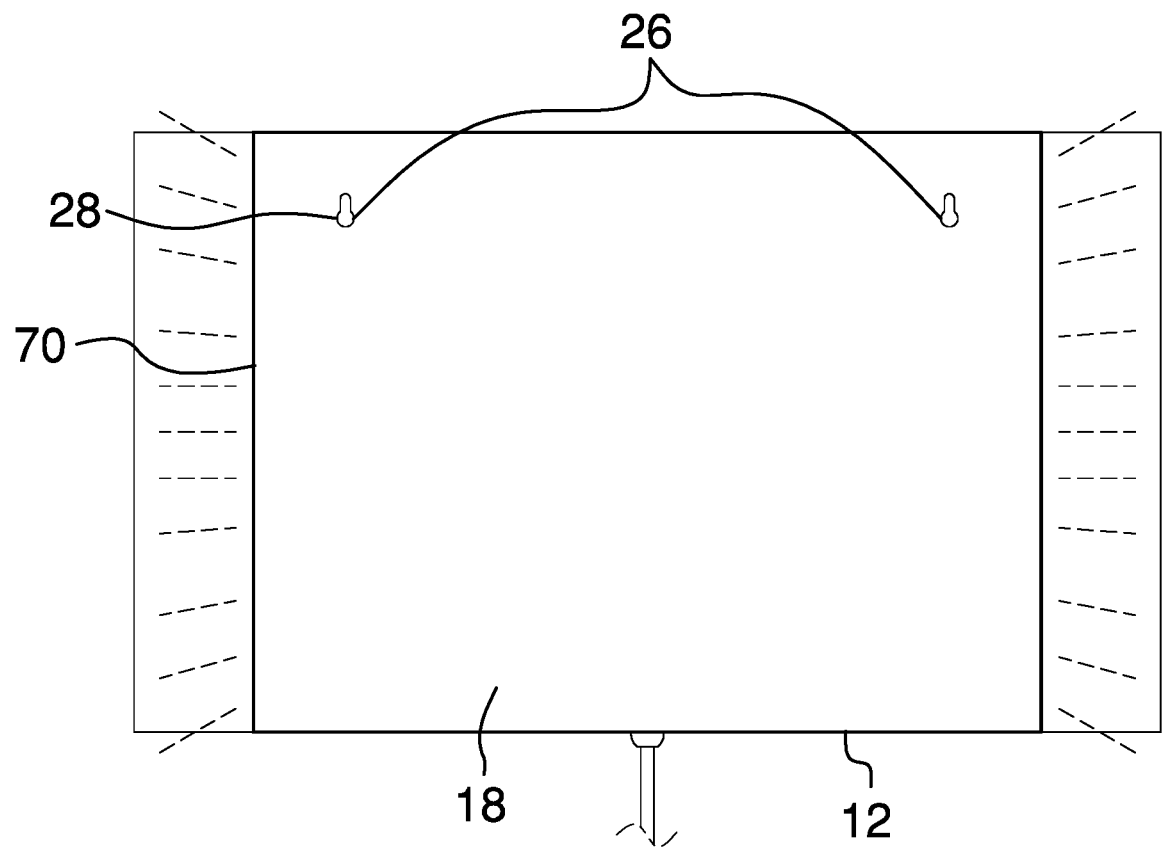
FIG. 6 is a back view of an embodiment of the disclosure.

A plurality of filters 38 is coupled to the housing 12 and is positioned in the interior space 14. The plurality of filters 38 comprises a primary filter 40 and a secondary filter 42, as shown in FIG. 4. The primary filter 40 and the secondary filter 42 are positioned so that the air that enters the interior space 14 passes first through the primary filter 40 and then through the secondary filter 42. The primary filter 40 comprises at least one of metal, polyester, polypropylene, and hog hair. The secondary filter 42 comprises at least one of paper, fabric, and fiberglass.

An orifice 44 is positioned in the bottom 24 of the housing 12 proximate to the filters 38, as shown in FIG. 3. The orifice 44 is configured to allow access to the interior space 14 to service the filters 38. A panel 46 is selectively couplable to the housing 12 to close the orifice 44. The primary filter 40 is intended for reuse as it can be removed via the orifice 44, cleaned, and reinserted into the interior space 14. The secondary filter 42 is intended for disposal when its use life has expired.

A blower module 48 is coupled to the housing 12 and is positioned in the interior space 14, as shown in FIG. 4. The blower module 48 is configured to draw the air through the first slots 30 and the filters 38. The air is filtered and expelled from the housing 12 through the second slots 32. The couplers 26 allow the housing 12 to be mounted to the vertical surface distal from the floor, which provides for more efficient filtering of the air.

The blower module 48 comprises a power module 50, a motor 52, and a fan 54. The motor 52 is operationally coupled to the power module 50. The fan 54 is coupled to a shaft 56 of the motor 52 so that the motor 52 is positioned to rotate the fan 54 concurrently with the shaft 56 to draw the air through the first slots 30 and the filters 38. The air is filtered and expelled from the housing 12 through the second slots 32.

The power module 50 comprises a cord 58 and a plug 60. The cord 58 is coupled to and extends from the bottom 24 of the housing 12. The plug 60 is coupled to the cord 58 distal from the housing 12. The plug 60 is configured to insert into a socket to operationally couple the blower module 48 to an electrical circuit.

A receiver 62 is coupled to the housing 12 and positioned in the interior space 14. The receiver 62 is operationally coupled to the power module 50. A plurality of speakers 64 is coupled to the housing 12. The speakers 64 are operationally coupled to the power module 50 and the receiver 62. The receiver 62 is configured to receive an audio signal from an electronic device of a user and to relay the audio signal to the speakers 64, positioning the speakers 64 to broadcast the audio signal to an area proximate to the housing 12 for entertainment. The plurality of speakers 64 comprises two speakers 64 that are coupled to the top 22 of the housing 12 singly proximate to the opposing sides 16.

A display 66, which is shaped complementarily to and coupled to the front 20 of the housing 12, is operationally coupled to the power module 50 and the receiver 62. The receiver 62 is configured to receive a video signal from the electronic device of the user and to relay the video signal to the display 66 to present to a person proximate to the housing 12 for entertainment. The display 66 is light emitting diode type.

A plurality of bulbs 68 is coupled to the housing 12 and is operationally coupled to the power module 50. The bulbs 68 are configured to provide backlighting when the housing 12 is coupled to the vertical surface and can serve as a nightlight 70. Each bulb 68 is coupled to a respective opposing side 16 of the housing 12 proximate to the front 20 of the housing 12, as shown in FIG. 3. Each bulb 68 comprises a light emitting diode 72.

In use, the housing 12 is mounted to the vertical surface. The blower module 48 draws the air through the first slots 30 and the filters 38. The air is filtered and expelled from the housing 12 through the second slots 32. When desired, the user can send the audio and video signals to be broadcast and displayed, respectively, by the speakers 64 and the display 66, to provide entertainment.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. An air purifying device comprising:
    a housing defining an interior space, the housing being substantially rectangularly box shaped, the housing having opposing sides, the opposing sides being recessed from the back of the housing to proximate to a front of the housing and from a top to a bottom of the housing, the front of the housing being convexly arcuate;
    a plurality of couplers coupled to a back of the housing wherein the couplers are configured for coupling the housing to a vertical surface;
    a set of first slots positioned in the housing wherein the first slots are configured for entering of air into the interior space;
    a set of second slots positioned in the housing wherein the second slots are configured for exiting of the air from the interior space;
    a plurality of filters coupled to the housing and positioned in the interior space; and
    a blower module coupled to the housing and positioned in the interior space wherein the blower module is configured for drawing the air through the first slots and the filters wherein the air is filtered and expelled from the housing through the second slots.

2. The device of claim 1, further including each coupler comprising a keyhole slot wherein the keyhole slot is configured for inserting an article of mounting hardware for coupling the housing to the vertical surface.

3. The device of claim 1, further including the plurality of couplers comprising two couplers.

4. The device of claim 1, further including the first slots and the second slots being louvered.

5. The device of claim 1, further comprising:
    the first slots being positioned in a first opposing side of the housing; and
    the second slots being positioned in a second opposing side of the housing.

6. The device of claim 1, further comprising:
    an orifice positioned in a bottom of the housing proximate to the filters wherein the orifice is configured for accessing the interior space for servicing the filters;
    a panel selectively couplable to the housing for closing the orifice; and
    the plurality of filters comprising a primary filter and a secondary filter, the primary filter and the secondary filter being positioned such that the air entering the interior space passes first through the primary filter and then through the secondary filter.

7. The device of claim 6, further comprising:
the primary filter comprising at least one of metal, polyester, polypropylene, and hog hair; and
the secondary filter comprising at least one of paper, fabric, and fiberglass.

8. The device of claim 1, further including the blower module comprising:
a power module;
a motor operationally coupled to the power module; and
a fan coupled to a shaft of the motor wherein the motor is positioned for rotating the fan concurrently with the shaft for drawing the air through the first slots and the filters wherein the air is filtered and expelled from the housing through the second slots.

9. The device of claim 8, further including the power module comprising a cord and a plug, the cord being coupled to and extending from a bottom of the housing, the plug being coupled to the cord distal from the housing wherein the plug is configured for inserting into a socket for operationally coupling the blower module to an electrical circuit.

10. The device of claim 8, further comprising:
a receiver coupled to the housing and positioned in the interior space, the receiver being operationally coupled to the power module; and
a plurality of speakers coupled to the housing, the speakers being operationally coupled to the power module and the receiver wherein the receiver is configured for receiving an audio signal from an electronic device of a user and for relaying the audio signal to the speakers for broadcasting to an area proximate to the housing.

11. The device of claim 10, further including the plurality of speakers comprising two speakers.

12. The device of claim 11, further including the speakers being coupled to a top of the housing singly proximate to the opposing sides.

13. The device of claim 8, further comprising:
a receiver coupled to the housing and positioned in the interior space, the receiver being operationally coupled to the power module; and
a display shaped complementarily to and coupled to a front of the housing, the display being operationally coupled to the power module and the receiver wherein the receiver is configured for receiving a video signal from an electronic device of a user and for relaying the video signal to the display for presenting to a person proximate to the housing.

14. The device of claim 13, further including the display being a light emitting diode.

15. The device of claim 1, further including a plurality of bulbs coupled to the housing, the bulbs being operationally coupled to the power module wherein the bulbs are configured for providing backlighting when the housing is coupled to the vertical surface.

16. The device of claim 15, further including each bulb being coupled to a respective opposing side of the housing proximate to the front of the housing.

17. The device of claim 15, further including each bulb comprising a light emitting diode.

18. An air purifying device comprising:
a housing defining an interior space, the housing being substantially rectangularly box shaped, the housing having opposing sides, the opposing sides being recessed from a back of the housing to proximate to a front of the housing and from a top to a bottom of the housing, the front of the housing being convexly arcuate;
a plurality of couplers coupled to the back of the housing wherein the couplers are configured for coupling the housing to a vertical surface, each coupler comprising a keyhole slot wherein the keyhole slot is configured for inserting an article of mounting hardware for coupling the housing to the vertical surface, the plurality of couplers comprising two couplers;
a set of first slots positioned in the housing wherein the first slots are configured for entering of air into the interior space, the first slots being louvered, the first slots being positioned in a first opposing side of the housing;
a set of second slots positioned in the housing wherein the second slots are configured for exiting of the air from the interior space, the second slots being louvered, the second slots being positioned in a second opposing side of the housing;
a plurality of filters coupled to the housing and positioned in the interior space, the plurality of filters comprising a primary filter and a secondary filter, the primary filter and the secondary filter being positioned such that the air entering the interior space passes first through the primary filter and then through the secondary filter, the primary filter comprising at least one of metal, polyester, polypropylene, and hog hair, the secondary filter comprising at least one of paper, fabric, and fiberglass;
an orifice positioned in a bottom of the housing proximate to the filters wherein the orifice is configured for accessing the interior space for servicing the filters;
a panel selectively couplable to the housing for closing the orifice;
a blower module coupled to the housing and positioned in the interior space wherein the blower module is configured for drawing the air through the first slots and the filters wherein the air is filtered and expelled from the housing through the second slots, the blower module comprising:
a power module, the power module comprising a cord and a plug, the cord being coupled to and extending from the bottom of the housing, the plug being coupled to the cord distal from the housing wherein the plug is configured for inserting into a socket for operationally coupling the blower module to an electrical circuit,
a motor operationally coupled to the power module, and
a fan coupled to a shaft of the motor wherein the motor is positioned for rotating the fan concurrently with the shaft for drawing the air through the first slots and the filters wherein the air is filtered and expelled from the housing through the second slots;
a receiver coupled to the housing and positioned in the interior space, the receiver being operationally coupled to the power module;
a plurality of speakers coupled to the housing, the speakers being operationally coupled to the power module and the receiver wherein the receiver is configured for receiving an audio signal from an electronic device of a user and for relaying the audio signal to the speakers for broadcasting to an area proximate to the housing, the plurality of speakers comprising two speakers, the speakers being coupled to the top of the housing singly proximate to the opposing sides;
a display shaped complementarily to and coupled to the front of the housing, the display being operationally coupled to the power module and the receiver wherein the receiver is configured for receiving a video signal from the electronic device of the user and for relaying the video signal to the display for presenting to a person proximate to the housing, the display being a light emitting diode; and a plurality of bulbs coupled to the housing, the bulbs being operationally coupled to the power module wherein the bulbs are configured for providing backlighting when the housing is coupled to the vertical surface, each bulb comprising a light emitting diode.

* * * * *